United States Patent [19]

Digby et al.

[11] Patent Number: 4,958,641
[45] Date of Patent: Sep. 25, 1990

[54] HEART DATA MONITORING METHOD AND APPARATUS

[75] Inventors: Dennis Digby, Wilsonville; Habib Homayoun, Aloha, both of Oreg.

[73] Assignee: Instromedix, Inc., Hillsboro, Oreg.

[21] Appl. No.: 321,736

[22] Filed: Mar. 10, 1989

[51] Int. Cl.$^5$ .............................................. A61B 5/04
[52] U.S. Cl. .................................... 128/702; 128/704
[58] Field of Search ............... 128/696, 702, 703, 903, 128/904, 704, 705, 706, 709, 710; 419/85

[56] References Cited

U.S. PATENT DOCUMENTS

| | | |
|---|---|---|
| 4,437,466 | 3/1984 | Saulson et al. ................. 128/419 PS |
| 4,667,682 | 5/1987 | Ihlenfeld, III ....................... 128/702 |
| 4,732,158 | 3/1988 | Sedeh .................................... 128/702 |

Primary Examiner—Francis Jaworski
Assistant Examiner—George Manuel
Attorney, Agent, or Firm—Kolisch, Hartwell & Dickinson

[57] ABSTRACT

Improved ambulatory heart data monitoring and recording apparatus and method are described. The apparatus provides a power partitioning and management circuit that enables the extended, continuous ECG monitoring of an ambulatory patient's cardiovascular performance and selective recording of arrhythmic events that transpire during such extended monitoring, wherein the circuit supplies reduced, unregulated DC power to potentially volatile data storage circuit elements in the event of the failure of the primary DC power source. An improved method validates QRS complexes by determining, during a learning period, characteristic criteria of the individual patient's QRS waveform most representative of a valid QRS complex as opposed to motion or other artifacts, and thereafter uses such learned criteria in heart rate monitoring. In another improved method, the occurrence of an arrhythmic event is determined by monitoring not only the patient's average heart rate relative to predetermined physiological norms but also the rate of change of the average heart rate, thereby reducing the likelihood that the apparatus gives false positive indications of abnormality.

6 Claims, 5 Drawing Sheets

HEART DATA MONITORING METHOD AND APPARATUS

BACKGROUND AND SUMMARY OF THE INVENTION

This invention relates generally to ambulatory heart monitoring methods and apparatus. More specifically, it concerns a QRS complex validation method and an arrhythmia identification method used in improved ambulatory ECG monitoring apparatus that, by virtue of its power partitioning and management circuit, can monitor continuously and event record a patient's cardiovascular performance for an extended period of time.

Typically, ambulatory heart rate monitoring and recording equipment rely upon volatile semiconductor read and write memory (RAM) devices to store ECG data for later analysis. As they usually are battery-powered, such equipment have a recording capacity limited by the RAM's density, as well as by the life of the batteries, which must power not only the RAM but also the microprocessor the analog to digital converter (ADC), the clock and other digital and analog circuitry. Twenty-four or forty-eight hour ambulatory cardiac monitoring equipment—while truly portable to the extent that they are lightweight and self-contained—are extremely limited in their ability to monitor arrhythmia, which may not manifest for days or even weeks.

Various methods for accurately detecting, or validating, QRS complexes (as against motion or other artifacts) within a patient's ECG signal have been used in ambulatory cardiac monitoring equipment. Most rely on some form of ECG signal amplitude measurement, at least over a candidate QRS interval, and comparison with presumed physiological norms. Similarly, methods for determining when a measured heart rate or change therein is worthy of recording as an arrhythmic event (as against a normal heart rate acceleration or deceleration) have depended upon comparisons of measured heart beat intervals with presumed physiologically normal heart rates. Methods which presume norms not always in evidence with a particular patient involved in a particular activity are intolerant of idiosyncratic, but perfectly acceptable, cardiovascular performance. Such methods thus are error-prone.

It is desired to provide in ambulatory heart rate monitoring equipment a greatly extended ECG monitoring and reporting capacity, without unduly burdening the ambulatory patient or restricting the patient's freedom to move about. It also is desired to provide improved techniques for detecting and validating QRS complexes, thereby to produce more accurate and reliable monitoring and recording results. Finally, it is desired to provide improved techniques for determining when an arrhythmic or other abnormal cardiovascular event has occurred, thus reducing the likelihood of a false positive indication of cardiovascular dysfunction.

Accordingly, it is a primary object of this invention to provide an ambulatory heart data monitoring and recording device capable of continuously monitoring and selectively recording a patient's cardiovascular performance over an extended period of time.

Another object of the invention is to provide such extended monitoring and recording capacity without further burdening or inconveniencing the ambulatory patient.

Yet another object of the invention is to provide such a device with a power partitioning and management circuit that ensures the long and uninterrupted supply of power to potentially volatile data storage circuit elements.

Still another important object of the invention is to provide a QRS complex validation technique that adapts itself to the individual patient.

Another important object of the invention is to provide an arrhythmic event determination technique that is less likely to give false positive indications of cardiovascular dysfunction.

A further object of the invention is to provide such improved heart rate monitoring and recording cost-effectively.

These and other objects of the invention will be understood in reference to the following detailed description of the preferred embodiment and methods of the invention, and by reference to the accompanying drawings.

DETAILED DESCRIPTION OF THE PREFERRED EMBODIMENT

Figure 1:
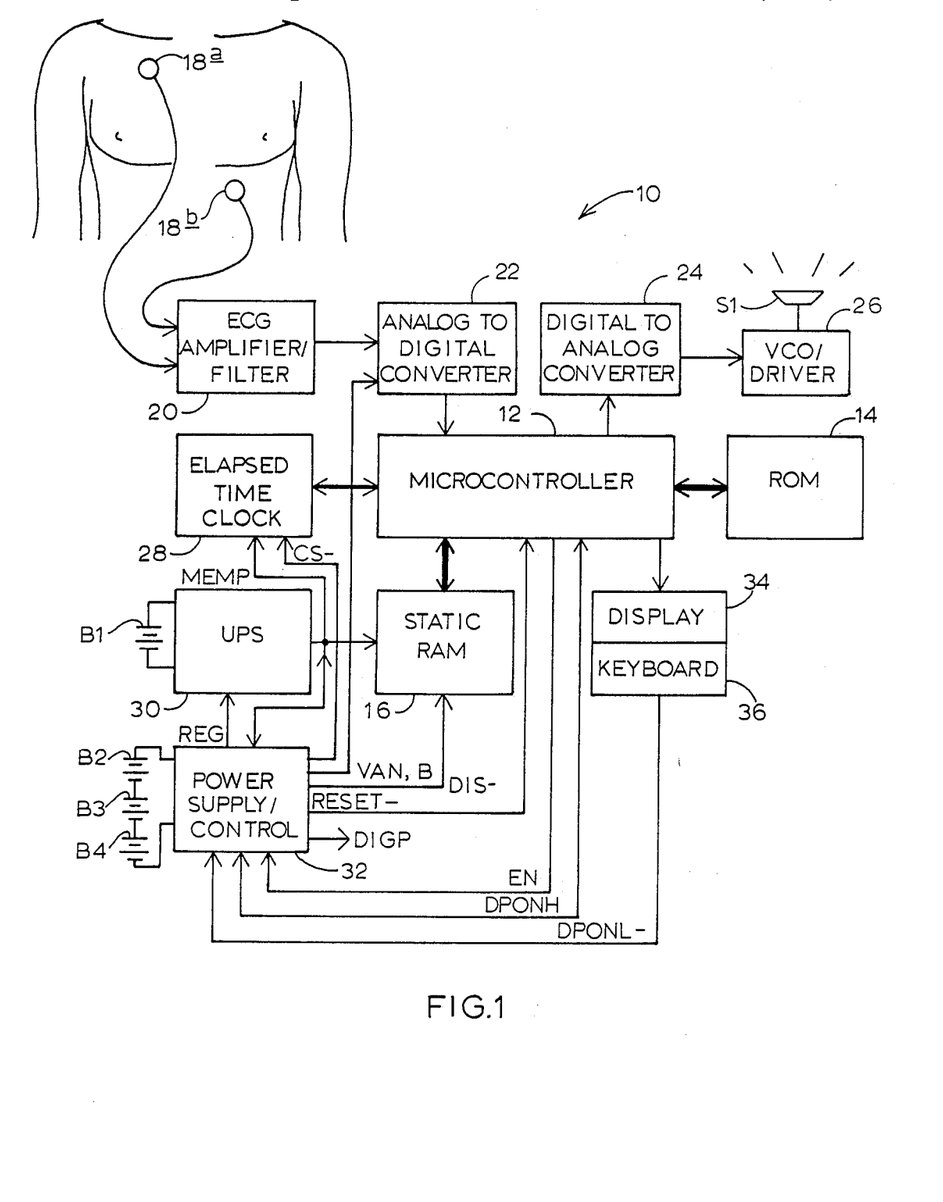
FIG. 1 is a simplified, schematic block diagram of the apparatus of the invention, made in accordance with its preferred embodiment.

Referring first to FIG. 1, a somewhat simplified, schematic block diagram of the apparatus of the invention, indicated generally at 10, is shown. In the interest of brevity and clarity, various details are intentionally omitted from FIG. 1, e.g. latches and drivers are not shown but will be understood by those skilled in the art to be required, depending upon the particular devices chosen to perform the required functions. Undisclosed hardware implementation details follow established design rules, and form no part of this invention. Signature conventions are used consistently herein to facilitate descriptions of signals and signal paths. Signatures consist of capitalized words or phrases that are believed to suggest a signal's function in the circuit being described. Signatures having a hyphen (-) as a suffix will be understood to be low-active.

Apparatus 10 is a lightweight, ambulatory, battery-powered device that is capable of measuring, recording and transmitting heart rate data to a remotely located physician for diagnosis, the data taking the form of digitized ECG signals. It is self-contained, requiring no external power, and conveniently can be carried upon the person of the patient. In its preferred embodiment, apparatus 10 can, for up to fourteen days, continuously monitor ECG data, and selectively record ECG data that correspond to detected cardiovascular abnormalities, e.g. arrhythmic "events." As will be seen, apparatus 10 provides the patient with the ability trans-telephonically to transmit data over standard phone lines, thus obviating a visit to the physician each time a monitoring session has ended.

Apparatus 10 includes computer means, or a microprocessor or microcontroller, 12; program storage means, or a read-only memory (ROM), 14; and a volatile memory device for data storage, or a static RAM, 16. In a manner that will be described below in reference to FIGS. 3 through 5, a program located in ROM 14 is executed by microcontroller 12 upon application of power via closure of a switch, and RAM 16 stores blocks of data pertaining to the patient's cardiovascular performance based upon ECG signal analysis. ECG signals are monitored by conventional probes, such as probes 18a, 18b, shown in FIG. 1 in the well-known "Lead II" position on a patient's chest.

Probes 18a, 18b provide a differential, analog signal representative of the dynamically changing electrical field on the skin surface of the patient. This analog signal is conditioned by ECG amplifier/filter 20 and converted (at a rate of approximately 109-Hz) by an ADC 22 into 8-bit digital values, which are input to microcontroller 12 via one of its data ports. A digital to analog converter (DAC) 24 and a voltage controlled oscillator (VCO)/driver circuit 26 enable frequency-shift-keyed (FSK) and frequency-modulated (FM) tones to be generated via speaker S1 for data communication to a remote site, as by placing a telephone transmitter adjacent a small hole provided in the enclosure of apparatus 10. The tone frequencies used in the preferred embodiment of the invention are nominally 1900- to 2500-Hz.

Referring still to FIG. 1, a programmable elapsed time clock 28 provides means for recording, with the ECG data, the total time that has elapsed from the moment when monitoring began, thus providing a relative indication of the time at which the reading was taken. As they must retain their otherwise volatile memory contents in the event of battery failure or excessive discharge, RAM 16 and clock 28 are powered by a backup, or uninterruptable, power supply (UPS) 30. This ensures that data are not lost when the power switch is turned off or when the primary power source is depleted.

Power supply means are provided in apparatus 10 by UPS 30 and power supply/control 32. DC power is supplied to UPS 30 by a single lithium battery B1 enabling UPS 30 to supply—without interruption and over the life of battery B1—a reduced level of unregulated voltage sufficient to sustain the potentially volatile data contents of RAM 16 and clock 28. Power supply/control 32 supplies RESET- to microcontroller 12, DIS- to RAM 16, CS- to clock 28, VAN and B to ADC 22 and DIGP to the remaining digital circuitry of apparatus 10. Power supply/control 32 also supplies REG to UPS 30 so that, should REG fall below a predetermined voltage level, UPS 30 continues without interruption to supply an unregulated, reduced DC voltage level to the volatile circuit elements. Alkaline batteries B2, B3, B4, which have a life of approximately fourteen days, are the primary source of DC power to power supply/control 32. A graphic liquid crystal display (LCD) 34 and a three-pushbutton keyboard 36 enable the physician or the patient to view selected parameters stored in ROM 14 or RAM 16 and, if desired, to change them. Closure of any of the pushbuttons of keyboard 36 produces a signal DPONL-, which is routed to power supply/control 32.

Those of ordinary skill in the art will appreciate that probes 18a, 18b; amplifier/filter 20; ADC 22; microcontroller 12; ROM 14; and RAM 16 provide detection means for detecting an abnormality in a patient's cardiovascular performance, wherein the abnormality may be defined as an event worthy of recording for later analysis by a physician. As will be seen below in reference to FIG. 4, a software routine that resides in ROM 14 and executes in microcontroller 12, e.g. the QRS complex validation routine, enables the detection means to analyze successive candidate QRS complexes based upon learned ECG signal slope data and predefined criteria, and to monitor the patient's heart rate. It also will be seen in reference to FIG. 5 that a software routine residing in ROM 14 and executing in microcontroller 12, e.g. the event definition routine described in detail below, provides event determination means integral with the detection means and responsive thereto for determining that an event has occurred.

An arrhythmic event such as bradycardia or tachycardia may be indicated by, respectively, too low or too high a sustained heart rate. Such arrhythmia are referred to herein as "events" and are, in the preferred embodiment of the invention, recorded as such in RAM 16. Thus, RAM 16 may be thought of as recordation means, integral with the determination means, for recording an event as ECG data representative thereof. Such data may be displayed, as by display 34, or transmitted, via DAC 24 and VCO/driver 26 trans-telephonically to a remote site for interpretation by a physician. Since static RAM 16 includes a volatile memory device in which the ECG data are stored, means must be provided to ensure that data are not lost in the event of power failure or the patient's inadvertent switching off of the power in apparatus 10. Such means including batteries B1, B2, B3, B4, UPS 30 and power supply/control 32 supply power to the detection means, the event determination means and the recordation means in a manner that now will be described.

Figure 2:
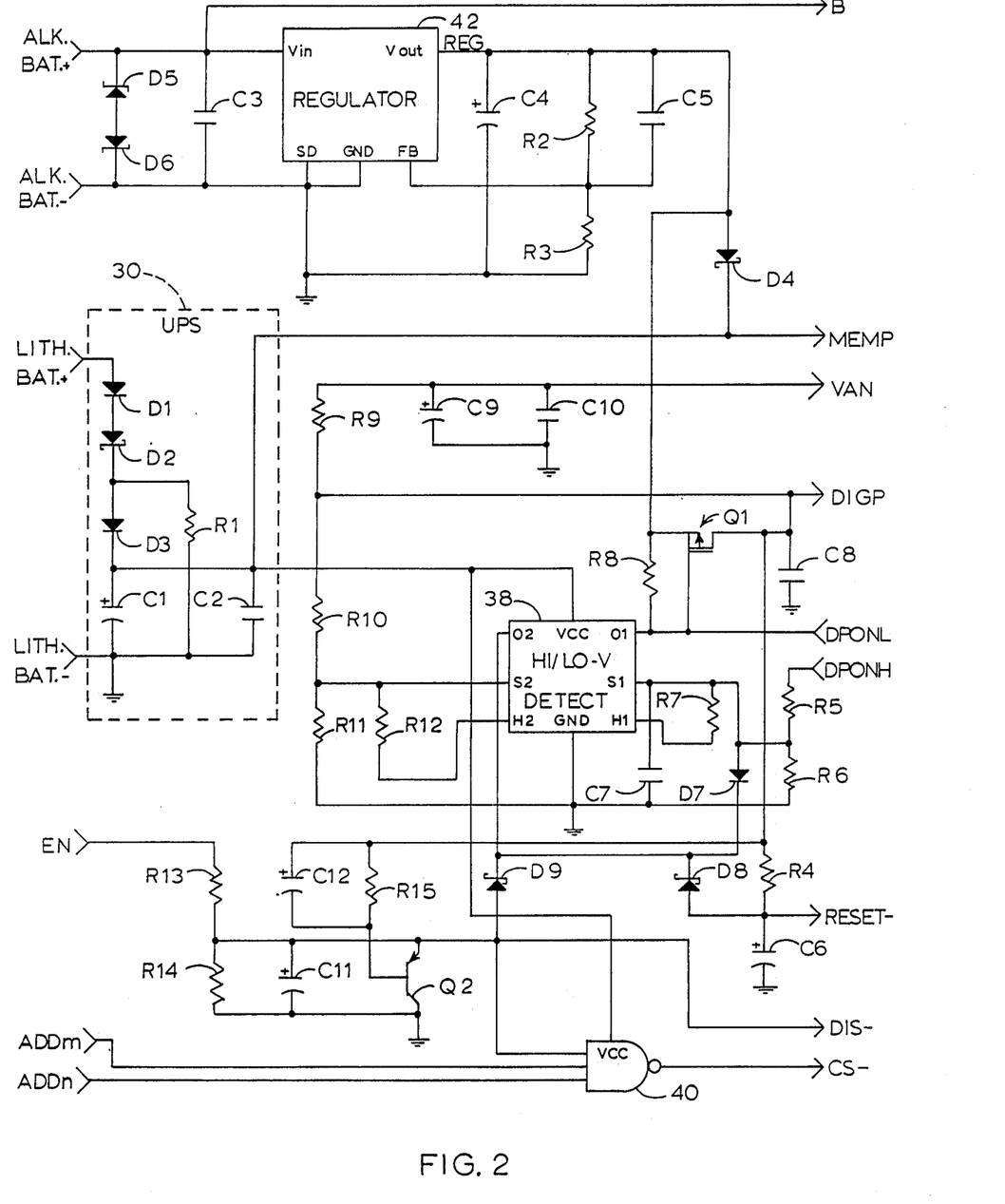
FIG. 2 is a detailed, schematic diagram of the power partitioning and management circuit in its preferred embodiment.

Turning to FIG. 2, UPS 30 and power supply/control 32 will be described in some detail, in order to point out an important feature of the present invention. UPS 30 includes connectors labeled LITH. BAT.+ and LITH. BAT.− representing the connection points of battery B1, which, in the preferred embodiment, provides nominally 3.6-V of DC power to UPS 30. Importantly, UPS 30 supplies a signal called MEMP to various circuit elements which are critical to the sustaining of data in static RAM 16. Thus, even if alkaline batteries B2, B3, B4 are removed from apparatus 10, e.g. for replacement, UPS 30 is capable of supplying MEMP at a minimum of 2.5-V—via voltage dropping diodes D1, D2, D3 and decoupling capacitors C1, C2—to reduce power consumption and to ensure that static RAM 16, which can operate down to 2.2-V, is within its data-sustaining operational range. A resistor R1 draws a minimum current from battery B1, in order to prevent the zero-current delay associated with lithium batteries. In the preferred embodiment, diodes D1, D3 are 1N4148; Schottky diode D2 has not only a low forward voltage drop, but also a low reverse current (e.g. HSMS-2820T30, which is available from Hewlett-Packard in Palo Alto, California, may be used); capacitor C1 is 22-$\mu$F; capacitor C2 is 0.1-$\mu$F; and resistor R1 is 2-M$\Omega$. Lithium battery B1 is chosen, in the preferred embodiment of the invention, for its ability to sustain its 3.6-V output until end-of-life, which in the preferred embodiment is approximately five to ten years.

Importantly, MEMP is used to supply DC power not only to static RAM 16, but also to certain circuit elements the operation of which must be sustained in order to maintain accurate ECG data and elapsed time information within the volatile circuit elements of apparatus 10. It is also important that the relatively high-capacity alkaline batteries B2, B3, B4, when installed in apparatus 10, supply most of the DC power to the circuitry of apparatus 10. Thus, MEMP alternatively is supplied, via a "wired-OR" connection, by power supply/control 32 via a Schottky diode D4. MEMP supplies nominally 2.5-V to an under/over-voltage detection circuit, or HI/LO-V detect circuit 38 (e.g. ICL7665BCBA, which is available from Intersil in Cupertino, California) and to a NAND gate 40. HI/LO-V detect circuit 38 provides the sequencing, upon the application of power to apparatus 10, of various DC power signals supplied by power supply/control 32. NAND gate 40 supplies a chip select signal CS- to elapsed time clock 28. Thus, even if alkaline batteries B2, B3, B4 are removed from apparatus 10, UPS 30 supplies sufficient power to sustain the volatile circuit elements, and associated driving or enabling circuit elements, for an extended period of time.

Connectors labeled ALK. BAT.+ and ALK. BAT.− provide the input to power supply/control 32 from alkaline batteries B2, B3, B4. Nominally, series connected batteries B2, B3, B4 supply 4.5-V to the input of a regulator 42. If this nominal battery voltage should exceed ±6.5-V, then one of two 6.2-V Zener diodes D5, D6 would break down and short out batteries B2, B3, B4. Zener diodes D5, D6 are connected back-to-back to prevent damage in the event that batteries B2, B3, B4 are installed with reverse polarity. An unregulated voltage B, decoupled by 0.1-$\mu$F capacitor C3 is routed (as shown in FIG. 1) to an input port of ADC 22, thereby allowing the alkaline batteries' voltages to be monitored by microcontroller 12. Those skilled in the art will appreciate that, should alkaline batteries B2, B3, B4 fall below a predefined voltage level, a "low battery" indication might be displayed on display 34, thus reminding the ambulatory patient that the batteries should be recharged or replaced.

Output REG of regulator 42 is set, by precision resistors R2, R3, nominally to 3.6-V, and is decoupled by decoupling capacitors C4, C5. In the preferred embodiment of the invention, resistor R2 is 750-k$\Omega$, 1%; resistor R3 is 383-k$\Omega$, 1%; capacitor C4 is 22-$\mu$F; and capacitor C5 is 0.1-$\mu$F. It will be understood that, while the circuitry shown in FIG. 2 will operate at unregulated voltages between 3.4-V and 5.7-V, regulator circuit 42 is used to drop voltage B to produce REG, thus reducing power consumption in apparatus 10. Schottky diode D4 drops REG by approximately 0.3-V to provide the "wired-OR" connection to MEMP. Thus, alkaline batteries B2, B3, B4 supply MEMP, and thus prolong the life of lithium battery B1, for as long as is possible, until REG drops to approximately 2.8-V.

Referring still to FIG. 2, the power sequencing circuitry and the generation of related logic and power signals will be described. In response to the application of power to apparatus 10 via keyboard 36, DPONL- momentarily goes active (low), which pulls the gate of a field effect transistor (FET) Q1 low, turning FET Q1 on and permitting DIGP and VAN to begin to rise toward REG's voltage level. When DIGP reaches approximately 3-V, the O2 output of HI/LO-V detect circuit 38 goes high impedance, permitting RESET- to go inactive after a delay set via a hysteresis output H1 by a 180-k$\Omega$ resistor R4 and a 1.0-$\mu$F capacitor C6. With microcontroller 12 no longer reset, execution of the apparatus' power up routine is possible, and DPONH is set to 1. After another delay set by resistors R5, R6, R7, an output O1 of HI/LO-V detect circuit 38 goes from its high impedance state to an active (low) state. This maintains the gate of FET Q1 low relative to its drain and turns FET Q1 on. Thus, DIGP and VAN continue to be supplied from REG via FET Q1 even after DPONL- returns to its normally inactive (high) state. In the preferred embodiment, resistors R5, R6, R7 are 1-M$\Omega$, 1-M$\Omega$, 10-M$\Omega$, respectively, a pull-up resistor R8 is 1-M$\Omega$ and a filter capacitor C7 is 0.047-$\mu$F. So long as FET Q1 is on, it has a forward voltage drop of only about 0.05-V at up to 8-mA of current, and thus is capable of supplying a voltage nearly equal to REG to the digital circuitry via DIGP (decoupled by a 0.1-$\mu$F capacitor C8) and to the analog circuitry via VAN (decoupled by a 100-$\Omega$ resistor R9 and 22-$\mu$F and 0.1-$\mu$F capacitors C9, C10), so long as batteries B2, B3, B4 are installed in apparatus 10 and not significantly discharged.

In the event that alkaline batteries B2, B3, B4 are removed or sufficiently discharged so that DIGP falls below a predefined threshold, e.g. 3-V, the set input S2 of HI/LO-V detect circuit 38 causes a second output O2 thereof to change from its high impedance state to a low active state in which DPONH is deactivated (pulled low) via a diode D7. The difference between the S2 input levels that cause O2 to switch is set via a hysteresis output H2 and resistors R10; R11; R12, which in the preferred embodiment are 1.00-M$\Omega$, 1%; 750-k$\Omega$, 1%; 10-M$\Omega$, respectively. HI/LO-V detect circuit 38 output O2 is connected as shown to Schottky diodes D8, D9, in order to reset microcontroller 12 and to disable RAM 16 and clock 28 via DIS when DIGP falls below 3-V. Output O2 is connected through diode D9 to one input of NAND gate 40 so that CS- is not "glitched" and the contents of clock 28 undesirably altered. It will be appreciated that the other inputs to NAND gate 40, namely address lines ADDm, ADDn, represent a mapping of clock 28's writable/readable registers into the addressable memory space of microcontroller 12.

In order to protect the data contents of RAM 16 during the switching by FET Q1 of DIGP (which otherwise may undesirably "glitch" the chip and output enable lines (CE- and OE-) of RAM 16), microcontroller 12 may set a signal EN upon power up and after reset. In the event that DPONH is pulled low by the O2 output of HI/LO-V detect circuit 38, microcontroller 12 would clear EN. EN is voltage-divided between a 100-k$\Omega$ resistor R13 and a 1-M$\Omega$ resistor R14, decoupled by a 1-$\mu$F capacitor C11 and connected to the emitter of a PNP transistor Q2. The base of transistor Q2 is driven, via a parallel resistor R15/capacitor C12 combination, by DIGP. Finally, the emitter of transistor Q2 is connected to the anode of Schottky diode D9. If DIGP should fall below 3-V, if DIGP should be "glitched", or if microcontroller 12 should clear EN, then DIS- goes inactive (high). Thus, DIS- may be used as an input to an inverting gate which drives the CE- and OE- inputs to the RAM devices represented in FIG. 1 by RAM 16. In this way data contents are not altered when power is being switched, when alkaline batteries B2, B3, B4 are removed with power on, or when the contacts among batteries B2, B3, B4 and the ALK. BAT.+ and ALK. BAT.—connectors undergo shock or vibration.

Referring still to FIG. 2, it may be seen that the power supply means includes a first power source, or power supply/control 32, and a second power source, or UPS 30, the first and second power sources being independently operable. Power supply/control 32 normally supplies power at at least a first predefined level, e.g. DIGP, to the detection means, the event determination means and the recordation means, while UPS 30 supplies a second predetermined level of power, e.g. MEMP, to the recordation means, or RAM 16, when power supply/control 32 fails to supply the first predetermined level of power. In this way, an event recorded as ECG data within a volatile memory device such as RAM 16 is preserved even in the event of the failure of the primary power source. As used herein, "failure" refers to a condition of discharge in alkaline batteries B2, B3, B4; their removal from apparatus 10, whether intentional or inadvertent (e.g. as a result of shock or vibration); or a catastrophic or other event in which one or more of the batteries effectively is taken out of the circuit by, for example, the breakdown of diodes D5 or D6 from static discharge.

It also may be seen that UPS 30 and power supply/control 32 are implemented in such manner that maximum power may be saved during the operation of apparatus 10, thereby significantly extending the period of time over which apparatus 10 may be used effectively to monitor a patient's ECG activity or cardiovascular performance. By the partitioning of the circuitry, as between those data storage devices, e.g. RAM 16 and clock 28 (which contain data that, once lost, is not recoverable), and the rest of the circuitry of apparatus 10, the invention provides unprecedented extended life and utility in ambulatory cardiac monitoring equipment.

The power supply means of apparatus 10 may be thought of as providing a first source of DC power having a predefined output voltage level (e.g. that of B) and a predefined nominal energy capacity; regulating the output voltage level to produce an operating voltage level (e.g. DIGP) that is lower than the output voltage level; and supplying the operating voltage level to at least one semiconductor device of the apparatus (e.g. the digital circuitry described in reference to FIGS. 1 and 2). In the preferred embodiment of the invention, the regulating is performed in such manner that the operating voltage (nominally 3.6-V) is substantially lower than a predefined nominal input supply voltage of such a semiconductor device (e.g. VCC=5-V). Thus, the predefined nominal energy capacity of such a source of DC power is increased to provide for extended ECG signal monitoring (e.g. for the extended life of alkaline batteries B2, B3, B4). The power supply means described above may be seen further to involve backing up the first source of DC power with a second source of DC power (e.g. UPS 30) operatively connected, in the event of the failure of such a first source of DC power, to a volatile memory device (e.g. static RAM 16) within the ambulatory ECG monitoring apparatus (e.g. apparatus 10). These power supplying methods yield the advantageous extended life, and thus extended utility, of ambulatory equipment, without adding great weight to apparatus 10, or requiring that the ambulatory patient remain near an auxiliary power source.

Figure 3:
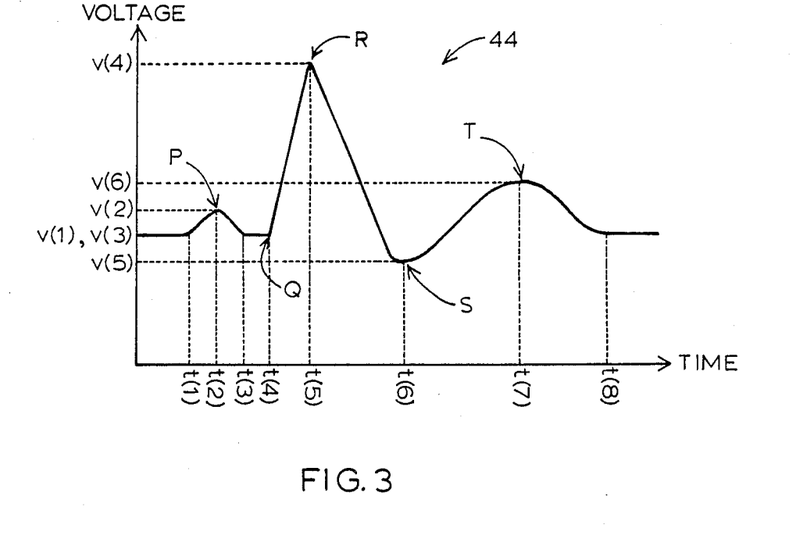
FIG. 3 is a graph of a typical QRS complex, which graph is useful in explaining the QRS validation method of the invention.

Turning now to FIG. 3, it will be appreciated by those skilled in the art that a typical PQRST waveform is indicated in graphic form generally at 44. Physiologically important P, Q, R, S and T maxima and minima are so indicated as being located, respectively, at coordinate pairs $(t(2),v(2)),(t(4),v(3)),(t(5),v(4)),(t(6),v(5))$ and $(t(7),v(6))$. It has been discovered that the slope of the ECG waveform reliably may be used to select an interval between adjacent P, Q, R, S or T points representative, for an individual patient, of a characteristic QRS complex. This phenomenon is exploited by the QRS validation method to improve the reliability of discriminating QRS complexes from noise and other artifacts, and to simplify QRS validation. It will be understood that the $t(n)$ and $v(n)$ points indicated, respectively, along the abscissa and ordinate of the graph in FIG. 3 are referred to herein as analysis points. They represent points believed to be of particular interest in validating QRS complexes, as will be seen in reference to FIG. 4. It will also be appreciated that conventional means, which forms no part of this invention, is used to respond to an end of conversion (EOC) signal from ADC 22; to read and smooth or otherwise filter the ADC data; to process the data with respect to recognition of amplitude inflections, maxima and minima corresponding to the analysis points; and to signal the QRS validation routine by incrementing the analysis point index n.

Figure 4:
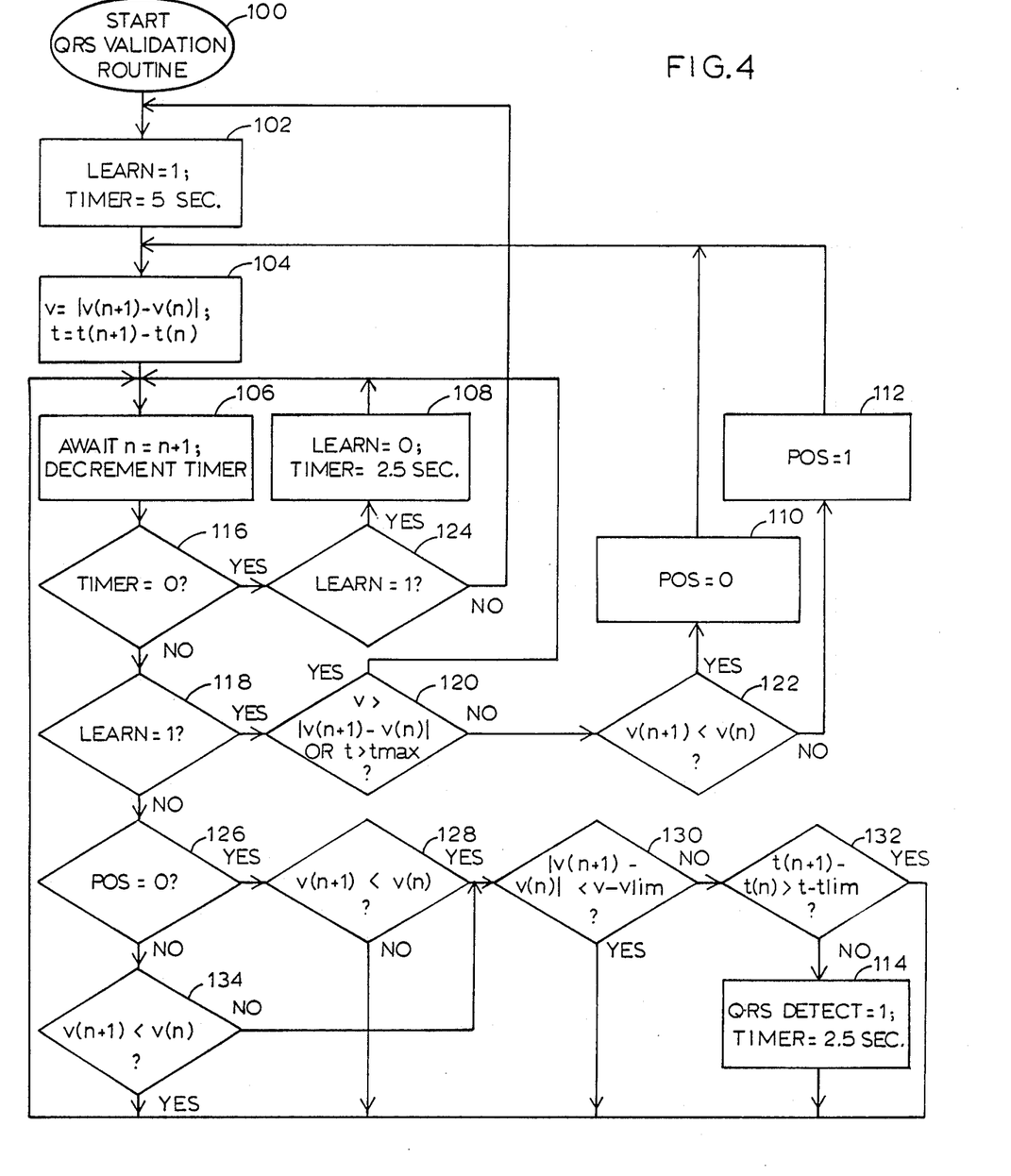
FIG. 4 is a flowchart of the QRS complex validation software routine as it is implemented in accordance with one of the preferred methods of the invention.

FIG. 4 is a flowchart of the QRS complex validation software routine implemented according to one of the preferred methods of the invention. It will be appreciated that diagramming conventions have been adopted, including a generally top-to-bottom and left-to-right directional flow. Ellipsis 100 indicates the entry point to the QRS VALIDATION ROUTINE. The rectangles indicate task or action blocks (e.g. action blocks designated 102, 104, 106, 108, 110, 112, 114). The rhombuses indicate decision blocks (e.g. decision blocks 116, 118, 120, 122, 124, 126, 128, 130, 132, 134), with the answer to the enclosed question determining the decisional path next taken. The flowchart of FIG. 4 is believed to be self-explanatory to persons skilled in the art, but will be described in some detail below.

The QRS validation routine is, by the preferred method of the invention, started upon power up of apparatus 10, at entry point 100. At 102 a boolean variable LEARN is initialized to 1 and a TIMER is set to the value in seconds of the learning period of time during which the patient's QRS waveform will be analyzed, or five seconds according to the preferred method. During this predefined learning period of time, the patient's ECG pattern is characterized by sampling, at the beginning $t(n)$ and the ending $t(n+1)$ of plural sampling intervals between successive analysis points in time (e.g. between $t(1)$ and $t(2)$, $t(2)$ and $t(3)$,...$t(7)$ and $t(8)$), the beginning $v(n)$ and the ending $v(n+1)$ amplitudes of the patient's ECG signal. During the learning period, at 120 the absolute value $|v(n+1)-v(n)|$ of the difference in amplitude between such points is compared with a predefined value v. If the measured change in amplitude is greater than or equal to v and if the elapsed time t between such points is less than or equal to a predefined maximum time Tmax, then control is transferred to 122. At 122, the sign of the change in amplitude is evaluated, thereby to determine whether the amplitude has increased or decreased during the interval between such points. If the sign of the amplitude change is positive, then a boolean variable POS is set to 1. Otherwise, POS is set to 0. In either case, the values of v and t are updated at 104 and the lapse of the next interval is awaited at 106.

At the end of the learning period, LEARN is set to 0 and TIMER is set to 2.5-s at 108. Those skilled in the art will appreciate that v now contains the absolute value of the highest voltage excursion over any learning period interval between successive analysis points; that t contains the value of the corresponding time duration; and that POS indicates whether the amplitude, or voltage excursion, over the same interval was positive or negative. Effectively, a learned rate of change of the patient's ECG signal is calculated, although by the preferred method the slope of the ECG waveform is not explicitly derived. (Persons skilled in the art will appreciate by reference to FIG. 3 that the slope of the waveform over, for example, the interval t(5)-t(4) would be (v(4)-v(3))/(t(5)-t(4)).)

After expiration of the learning period, the validity of candidate QRS complexes may be determined during what is referred to herein as successive monitoring periods. In accordance with the preferred method of the invention, this is done by calculating a measured rate of change of the ECG signal, e.g. at 126, 128, 130, 132, 134, and comparing the measured rate of change with the rate of change that has been previously learned, e.g. at 130, 132. If the absolute value of the measured voltage excursion over any interval between successive analysis points is greater than or equal to the difference between the learned rate of change and a predefined $\Delta v$, or vlim, then control is transferred from 130 to 132. At 132, the measured time between such points is compared to the sum of the learned time duration and a predefined $\Delta t$, or tlim. If the measured voltage excursion is greater than or equal to a learning period-based minimum excursion, and if the measured time corresponding to the measured voltage excursion is less than a learning period-based maximum time duration, then the candidate QRS complex is determined to be valid, and at 114 a boolean variable QRS DETECT is set to 1. TIMER is reinitialized to 2.5-s, and monitoring continues.

It is noted that, whether in the learning period or the monitoring period, the learning period may be restarted. This is illustrated at 124, where it is determined whether TIMER equals 0 (either a learning period of 5-s has elapsed or a monitoring period of 2.5-s has lapsed) and, if so, then whether LEARN equals 1. If TIMER equals 0 and LEARN equals 1, then the learning period is over, and a monitoring period begins. If TIMER equals 0 and LEARN equals 0, then 2.5-s of monitoring has indicated no valid QRS complex (otherwise, TIMER would have been reinitialized at 114), and a new learning period is begun by transfer of control to 102.

Thus the preferred QRS validation method of the invention is understood. By the preferred method, the learning period (and relearning period) is 5-s, and successive monitoring periods thereafter are 2.5-s, in duration. Voltage and time tolerances have been determined preferably to be tmax=46-ms, vlim=v/4 and tlim=t, and the preferred initial values for v and t (the first time through action block 104) are, respectively, tmax (or 46-ms) and vmax/256, or approximately 15.5-$\mu$V. It will be appreciated that other times and tolerances may, within the spirit of the invention, be utilized to achieve the patient-adaptive monitoring advantages of the invention in which an individual patient's particular cardiology is accommodated by characterizing the ECG signal and comparing subsequent cardiovascular performance based upon such an individualized characterization. The cardiology of a patient whose ECG signal characteristically exhibits, for example, a higher Q-R segment voltage excursion than R-S segment voltage excursion (the reverse of that shown in FIG. 3), thus is as easily and reliably monitored by apparatus 10 as that of a patient having what may thought to be a more physiologically "normal" ECG signal.

The preferred QRS validation method may be summarized as including the steps of (1) characterizing a patient's ECG signal, or pattern, by sampling at the beginning and the ending of plural sampling intervals between successive, predefined analysis points (e.g. t(n) in FIG. 3), for a predefined learning period of time and calculating a learned rate of change thereof over such intervals; and, thereafter, (2) determining the validity of QRS complexes by sampling between such points the ECG signal, calculating a measured rate of change thereof and comparing the measured rate of change with the learned rate of change.

Stated in other words, the preferred QRS validation method includes the steps of (1) sampling an ECG signal to produce data representing the ECG signal amplitudes at the beginning and ending of a sampling interval between predefined analysis points; (2) calculating the magnitude (e.g. $|v(n+1)-v(n)|$) and the direction (POS) of the change in signal amplitude over the interval, the magnitude being equivalent to the magnitude result of subtracting (e.g. at 120) the signal amplitude at the beginning of the interval (e.g. v(n)) from the signal amplitude at the end thereof (e.g. v(n+1)) and the direction of the change being equivalent to the sign result (e.g. POS=0 or 1) of such subtracting; (3) repeating the sampling and calculating steps (e.g. at 106, 118, 120, 122) for a predefined learning period of time including plural ones of such intervals (e.g. t(1) to t(2), t(2) to t(3),...t(7) to t(8)); (4) comparing the magnitudes of the changes in the ECG signal amplitude (e.g. at 120, 104) to determine the magnitude (e.g. $v=|v(n+1)-v(n)|$) and the direction (POS) of the greatest change in ECG signal amplitude over the learning period; and thereafter (5) identifying QRS complexes within such ECG signal by comparing, with the magnitude of the greatest change, the magnitudes of only those changes in the ECG signal amplitude which are of the same direction as that of such greatest change (e.g. at 126, 128, 130, 134, 114).

Figure 5:
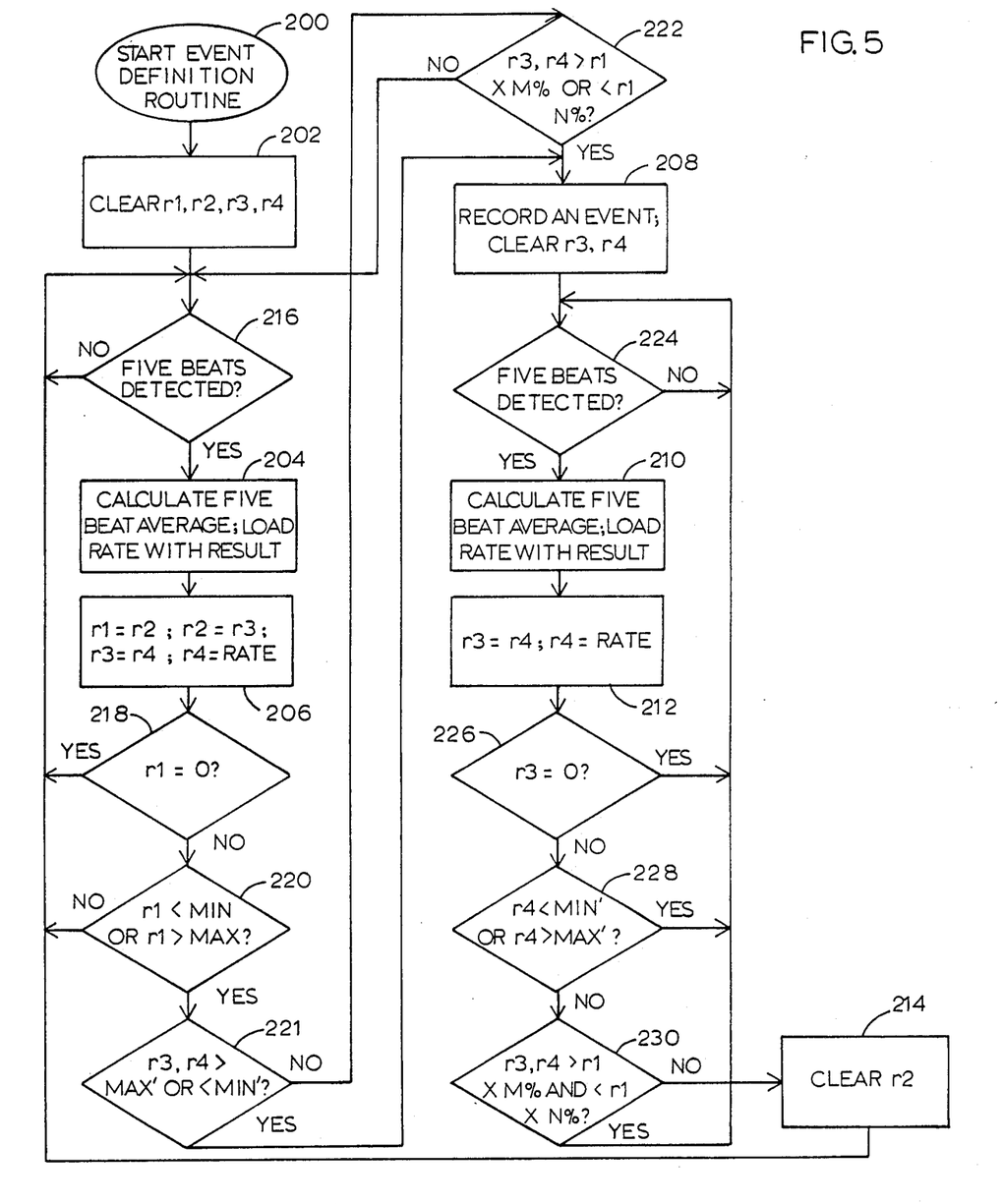
FIG. 5 is a flowchart of the arrhythmia identification software routine as it is implemented in accordance with another preferred method of the invention.

Turning finally to FIG. 5, a flowchart of the event definition software routine implemented according to another preferred method of the invention is shown. The flowchart of FIG. 5 complies with the same conventions mentioned above in reference to FIG. 4, and consists of an entry point designated 200 and indicated by an ellipse; action blocks designated 202, 204, 206, 208, 210, 212, 214 and indicated by rectangles; and decision blocks 216, 218, 220, 221, 222, 224, 226, 228, 230 and indicated by rhombuses. The flowchart of FIG. 5 is believed to be self-explanatory to persons skilled in the art, but will be described in some detail below.

The event definition routine whose entry point is designated 200 and which may be executed within microcontroller 12 as a task that runs concurrently with the other data collection and processing tasks mentioned above. The event definition routine is best described as including the steps of detecting a patient's heartbeat, calculating heart rate averages, comparing the averages with predefined constant threshold values, comparing the averages with one another and evaluating the result of the former and latter comparing steps in accordance with predefined criteria to identify arrhythmic events. These steps are illustrated in the flowchart of FIG. 5 at 216, 204, 206, 218, 220, 221, 222, 208. The remaining portion of the software illustrated in the flowchart in FIG. 5, designated 224, 210, 212, 226, 228, 230, 214, will be understood simply to await the return of the patient's heart rate to a quiescent condition following an arrhythmic event, thereby to avoid the possibility of double recording a single event.

In essence, registers r1, r2, r3, r4 are arranged as a shiftable array, or queue, of predefined depth. They store successive, calculated, five beat running averages representing the patient's heart rate. As soon as four such running averages have been calculated and 'shifted' into registers r1, r2, r3, r4 (when register r1, which was originally cleared, is no longer equal to zero as determined at 218), then the oldest such average, which resides in register r1, is compared to two predefined, constant, threshold values MIN, MAX. In the preferred embodiment, MIN and MAX are, respectively, approximately 45-beats-per-minute (bpm) and 125-bpm. If the five beat average residing in register r1 is less than MIN, a candidate bradycardia condition exists; if the oldest five beat average is greater than MAX, then a candidate tachycardia condition exists. At 221, more recent running averages in registers r3, r4 are compared to a second set of predefined, constant, threshold values MIN', MAX'. According to the preferred embodiment, if the values in both registers r3 and r4 are greater than 200-bpm or less than 30-bpm, then control is transferred to action block 208 to record an event. In such an extreme case, arrhythmia may be assumed to have occurred.

Importantly, arrhythmic event definition does not end with such comparisons to what might be thought of as presumed physiological norms. Instead, by the preferred method of the invention (and assuming that a candidate arrhythmic condition exists but that it is not so extreme as to be presumptively worthy of recording as an event), further comparisons are made between various of the stored heart rate averages. At 222 the oldest average, which resides in register r1 and has been determined to be either less than MIN or greater than MAX, is compared to the two more recent five beat averages residing in registers r3, r4. By the preferred method of the invention, only if both more recent averages are greater than 165% or less than 35% of the value of the oldest stored five beat average is an event recorded by transfer of control from decision block 222 to action block 208. Otherwise, no arrhythmic event is recorded, despite the fact that a calculated five beat average was outside of what might have been thought to be an acceptable bpm range between MIN and MAX.

It will be appreciated that, within the spirit of the invention, MIN, MAX, MIN' and MAX' may be set at any suitable lower and upper limits and that M and N may be set to other than one hundred sixty-five and thirty-five, respectively. It also will be appreciated that greater or fewer than five beats may be included in the calculated average, and that a greater or fewer number of registers in the array may be used, depending upon the desired 'noise immunity' and sensitivity of the arrhythmia detection technique. Finally, it will be appreciated that by the preferred method of the invention, an effective rate of change of said averages over a predefined number of detected heart beats is determined, which rate of change is compared with a predefined threshold value, as a result of the pair-wise comparison of the beat averages contained in registers r1, r3 and r1, r4. Thus, it will also be appreciated that this determination and comparison of the rate of change to identify arrhythmia may be done by comparison to absolute threshold values, e.g. 1-bpm/s, or, in accordance with the preferred method, compared in relative terms to previously stored averages.

At 208, registers r3, r4 are cleared. At 224, 210, 212, two successive calculated five beat averages are stored, and these more recent averages are compared, almost identically as before at 220, 222, with the oldest stored average. When the running average value in register r4 is determined at 228 to be between MIN' (e.g. 30-bpm) and MAX' (e.g. 200-bpm) and when a subsequent pair of successive, five beat averages is determined at 230 to be between 35% and 165% of the oldest stored five beat average, then register r2 is cleared at 214 and control is transferred to 216. There, another five beat average is calculated and, once again, successive averages are 'shifted' in time along the register array, or pushed onto the queue, and it is determined by a pair-wise comparison whether at least one, and preferably two, of the averages is within a predefined percentage of at least one other.

Thus, the preferred event definition method of the invention is seen to achieve the claimed advantages. Rather than relying on sometimes misleading results of comparison of a patient's heart rate with presumed physiological norms, the present event definition method produces more reliable results based upon comparison of running heart rate averages with physiological norms, and further, and more importantly, based upon plural, pair-wise comparisons between such running heart rate averages, thereby effectively evaluating also the rate of change of the patient's heart rate. It has been found that such a method produces more reliable identification of arrhythmia, and is less likely to produce false positive indications of cardiac abnormality or dysfunction. Finally, it may be seen that the preferred event definition method is patient-adaptive, since the running heart rate average comparisons are based not upon potentially erroneous assumptions, but rather upon an individual patient's own recent heart rate history.

The objects of the invention thus are realized. Improved, extended, continuous, ambulatory cardiac monitoring is made possible by the power partitioning and management apparatus and method disclosed herein in which a primary source of power may be switched on and off dependent upon the presence and capacity of removable alkaline batteries, without the loss of important ECG data stored in volatile circuit elements. Power is saved, thereby to extend the period in which the patient's ECG signal may be monitored and events recorded, by regulating down the voltage level available from the primary and backup DC power supplies to a level substantially below the rated operating voltage level of the digital circuitry to which DC power is supplied. QRS complex validation is simplified and rendered more reliable by a patient-adaptive technique in which the patient's ECG signal is monitored during a learning period of time; the ECG signal is characterized, based upon predefined criteria such as the greatest voltage excursion in the ECG waveform; and thereafter the patient's ECG signal is monitored and QRS complexes are validated based upon the criteria developed during the learning period. Finally, arrhythmic events are more reliably identified, for recording and further analysis, based not only upon 'raw' heart rate data, but also upon the rate of change of the patient's heart rate, thereby reducing the likelihood of giving a false positive indication of heart rate abnormality.

Accordingly, while preferred methods for practicing the invention, and a preferred embodiment of the apparatus of the invention, have been described herein, it is appreciated that further modifications are possible that come within the scope of the invention.

What is claimed and desired to secure by letters patent:

1. For use in ECG monitoring apparatus, a patient-adaptive QRS complex validation method comprising:
   characterizing a patient's ECG pattern by sampling at the beginning and the end of plural sampling intervals between predefined analysis points an ECG signal for a predefined learning period of time and calculating a learned rate of change of such ECG signal over said intervals, and thereafter
   determining the validity of QRS complexes by sampling between such analysis points such ECG signal, calculating a measured rate of change of such ECG signal and comparing said measured rate of change with said learned rate of change.

2. A patient-adaptive ECG monitoring method comprising:
   sampling an ECG signal to produce data representing the ECG signal amplitudes at the beginning and the end of a sampling interval between predefined analysis points;
   calculating the magnitude and the direction of the change in the signal amplitude over said interval, said magnitude of the change being equivalent to the magnitude result of subtracting the signal amplitude at the beginning of said interval from the signal amplitude at the end of said interval and said direction of the change being equivalent to the sign result of such subtracting;
   repeating the sampling and calculating steps for a predefined learning period of time including plural ones of said intervals;
   comparing the magnitudes of the changes in the ECG signal amplitude to determine the magnitude and the direction of the greatest change in ECG signal amplitude over said learning period; and thereafter
   identifying QRS complexes within such ECG signal by comparing with the magnitude of said greatest change the magnitudes of only those changes in the ECG signal amplitude which are of the same direction as the direction of said greatest change.

3. For use in ambulatory ECG monitoring apparatus, an arrhythmia identification method comprising:
   detecting a patient's heart beats;
   calculating plural running heart rate averages; constant threshold value to produce a first comparison result;
   comparing said averages with one another to produce a second comparison result representing a rate of change of said averages; and
   evaluating said first comparison result and said second comparison result, in accordance with predefined criteria, to identify arrhythmia.

4. For use in ambulatory ECG monitoring apparatus, an arrhythmia identification method comprising:
   detecting a patient's heart beats;
   calculating plural running heart rate averages, each of said averages being based upon a first predefined number of detected heart beats;
   first comparing said averages with at least one of a predefined maximum value and a predefined minimum value;
   determining a rate of change of said averages over a second predefined number of detected heart beats;
   second comparing said rate of change with a predefined threshold value; and
   identifying arrhythmia based upon one of said averages being greater than said predefined maximum or less than said predefined minimum value and said rate of change being greater than said predefined threshold value.

5. The method of claim 4, wherein said determining and said second comparing steps are performed by the pair-wise comparison of at least two of said averages.

6. The method of claim 5, wherein said averages are stored in a queue of predefined depth, said queue being pushed with successive ones of said averages, wherein said pair-wise comparison is performed by determining whether at least one of said averages is within a predefined percentage of at least one other of said averages.

* * * * *

UNITED STATES PATENT AND TRADEMARK OFFICE
CERTIFICATE OF CORRECTION

PATENT NO.    : 4,958,641

DATED         : September 25, 1990

INVENTOR(S)   : Dennis Digby and Habib Homayoun

It is certified that error appears in the above-identified patent and that said Letters Patent is hereby corrected as shown below:

Please correct claim 3 to include the underscored language which the Office omitted:

3. For use in ambulatory ECG monitoring apparatus, an arrhythmia identification method comprising:

detecting a patient's heart beats;

calculating plural running heart rate averages;

<u>comparing said averages with at least one predefined constant</u> threshold value to produce a first comparison result;

comparing said averages with one another to produce a second comparison result representing a rate of change of said averages; and     evaluating said first comparison result and said second comparison result, in accordance with predefined criteria, to identify arrhythmia.

Signed and Sealed this

Tenth Day of December, 1991

*Attest:*

HARRY F. MANBECK, JR.

*Attesting Officer*       *Commissioner of Patents and Trademarks*